United States Patent [19]

Lacome et al.

[11] Patent Number: 5,698,501
[45] Date of Patent: Dec. 16, 1997

[54] ETHYLENIC HYDROCARBONS SULPHURIZED BY ELEMENTAL SULPHUR IN THE PRESENCE OF AN ALKALI METAL CARBONATE OR BICARBONATE, THEIR PREPARATION AND THEIR USE

[75] Inventors: Thierry Lacome, Rueil Malmaison; Bruno Delfort, Paris; Maurice Born, Nanterre, all of France

[73] Assignee: Institut Francais Du Petrole, Rueil-Malmaison, France

[21] Appl. No.: 584,198

[22] Filed: Jan. 11, 1996

[30] Foreign Application Priority Data

Jan. 10, 1995 [FR] France ................. 95 00282

[51] Int. Cl.$^6$ .......................... C10M 135/04
[52] U.S. Cl. ................. 508/322; 508/342; 568/18
[58] Field of Search ......................... 508/322

[56] References Cited

U.S. PATENT DOCUMENTS

| | | | |
|---|---|---|---|
| 3,673,090 | 6/1972 | Waldbillig et al. | 252/45 |
| 3,882,031 | 5/1975 | Askew et al. | 508/280 |
| 4,097,474 | 6/1978 | Askew et al. | 549/31 |
| 4,119,549 | 10/1978 | Davis | 508/324 |
| 4,225,488 | 9/1980 | Horodysky et al. | 252/45 |
| 4,284,520 | 8/1981 | Bolle et al. | 568/21 |
| 4,584,113 | 4/1986 | Walsh | 252/45 |
| 4,739,036 | 4/1988 | Colvin et al. | 528/389 |
| 4,983,558 | 1/1991 | Born et al. | 502/31 |
| 5,133,889 | 7/1992 | Born et al. | 508/322 |
| 5,135,670 | 8/1992 | Johnson et al. | 252/45 |
| 5,232,623 | 8/1993 | Shaw | 252/183.18 |
| 5,286,395 | 2/1994 | Born et al. | 252/45 |
| 5,338,468 | 8/1994 | Arvizzigno et al. | 252/45 |
| 5,403,960 | 4/1995 | Kadkhodayan et al. | 568/21 |
| 5,410,088 | 4/1995 | Harris et al. | 568/21 |

FOREIGN PATENT DOCUMENTS

| | | |
|---|---|---|
| 0 130 850 | 1/1985 | European Pat. Off. . |
| 0 201 197 | 11/1986 | European Pat. Off. . |
| 0 258 168 | 3/1988 | European Pat. Off. . |
| 1211610 | 8/1958 | France . |
| 734 249 | 5/1980 | U.S.S.R. ......... C10M 135/04 |
| 748 694 | 6/1953 | United Kingdom . |
| 1 067 378 | 5/1967 | United Kingdom . |
| 1 404 714 | 9/1975 | United Kingdom . |

OTHER PUBLICATIONS

Chemical Abstract, vol. 100(18), Abstract No. 142011m, 20 Apr. 1984.

Primary Examiner—Ellen M. McAvoy
Attorney, Agent, or Firm—Millen, White, Zelano, & Branigan, P.C.

[57] ABSTRACT

Sulphur-containing substances are derived from mono- or polyethylenic hydrocarbons by sulphurization using elemental sulphur in the presence of an alkali metal carbonate or bicarbonate and in the presence of water and/or at least one alkyleneglycol.

The sulphur-containing substances, which may contain 20% to 70% by weight of sulphur, are generally soluble in lubricants to improve antiwear and extreme pressure properties. They can also be used as sulphurization agents, in particular for preparing catalysts for refining petroleum products.

4 Claims, No Drawings

ETHYLENIC HYDROCARBONS SULPHURIZED BY ELEMENTAL SULPHUR IN THE PRESENCE OF AN ALKALI METAL CARBONATE OR BICARBONATE, THEIR PREPARATION AND THEIR USE

BACKGROUND OF THE INVENTION

The invention concerns novel sulphur-containing organic substances, a process for their preparation and their use.

Various sulphur-containing organic substances have long been used as additives for lubricants, in particular to improve antiwear and extreme pressure properties. In particular, they are used in lubricants for highly loaded gears or metal working lubricants.

Sulphur-containing organic substances for use as antiwear and extreme pressure additives have been widely described and are obtained by various processes, which principally comprise the following two steps:

1) forming an addition product between a sulphur chloride (sulphur mono- or dichloride) and a compound containing an ethylenic unsaturation; and
2) reacting this addition product with a sulphur-containing product: a sulphide, hydrosulphide or polysulphide of an alkali metal (for example sodium) used as is or formed in situ by reacting hydrogen sulphide ($H_2S$) or mercaptans with an alkali metal hydroxide (for example sodium hydroxide).

In order to increase the sulphur content in the substances obtained, elemental sulphur can be used during the second step described above.

Because chlorine-containing compounds are used in the first step of the preparation, sulphur-containing substances of this type always contain a certain residual amount of chlorine. Various improvements to the process, in particular our own, have been able to reduce this to less than 250 ppm over the past few years. In addition, these processes cause formation of alkali metal chlorides (generally NaCl) and water-soluble organic alkaline derivatives as by-products, which are recovered in large quantities as highly polluting aqueous solutions which are thus very expensive to eliminate.

A number of processes for the preparation of sulphur-containing substances which do not use chlorine-containing compounds is known. Some of these processes involve the sulphurization of olefins by elemental sulphur and hydrogen sulphide ($H_2S$). These processes have the drawback of using a highly toxic reactant which is difficult to store and transport, and the processes develop very high pressures which can reach 90 bars, for example.

Other processes use elemental sulphur and alkaline or alkaline-earth hydrosulphides.

SUMMARY OF THE INVENTION

We have now discovered that it is possible to prepare sulphur-containing substances from mono- or polyethylenic hydrocarbons using elemental sulphur as the sole sulphur-containing reactant by operating in the presence of at least one alkali metal carbonate or bicarbonate and in the presence of water in a proportion of 50 to 500 $cm^3$ per ethylenic unsaturation in the hydrocarbon, and/or in the presence of at least one alkyleneglycol.

The sulphur-containing substances of the invention are free of chlorine, and generally have a sulphur content which can reach about 20% to 70% by weight, depending on the starting ethylenic hydrocarbon. The sulphur-containing substances of the invention are soluble to different degrees in mineral oils and in hydrogenated polyalphaolefins, even— and this is completely unexpected—those substances with a high sulphur content.

The sulphur-containing substances of the invention can generally be defined by the fact that they are obtained by reacting at least one mono- or polyethylenic hydrocarbon which generally contains 2 to 36 carbon atoms and 1 to 3 ethylenic unsaturations with a suitable quantity of elemental sulphur in the presence of at least one alkali metal carbonate or bicarbonate and in the presence of water and/or at least one alkyleneglycol.

The starting mono- or polyethylenic hydrocarbons may be open chain, linear or branched, or cyclic. Examples are ethylene, propylene, 1-butene, n-butenes, isobutene, the pentenes, the hexenes (for example 2,3-dimethyl 1-butene), 1,3-butadiene, isoprene, cyclopentadiene, dicyclopentadiene, dimers and trimers of isobutene, trimers and tetramers of propylene, and non hydrogenated polyalphaolefins with low molecular weights (for example, up to about 500). Isobutene is preferably used.

In the reaction preparing the sulphur-containing substances of the invention, up to about 250 g (i.e., about 8 moles) of elemental sulphur per ethylenic unsaturation can be used in the starting hydrocarbon.

Water is also introduced into the reaction medium in a proportion of 50 to 500 $cm^3$ per ethylenic unsaturation in the starting hydrocarbon, and/or an alkyleneglycol such as ethyleneglycol or propyleneglycol, in a proportion which can, for example, be in the range 10 g to 150 g per ethylenic unsaturation in the starting hydrocarbon.

Particular alkali metal carbonates and bicarbonates are those of lithium, sodium and potassium. Sodium or potassium is most frequently used. The proportion of carbonate or bicarbonate used can be in the range $3 \times 10^{-3}$ to 1.2 moles per ethylenic unsaturation in the starting hydrocarbon.

Surprisingly, the alkali metal carbonate or bicarbonate can be used in very low proportions (quasi catalytic) and the sulphur-containing substances finally produced contain no alkali or alkaline-earth metals and are not basic. It may be that the carbonate or bicarbonate acts as a promoter for the sulphurization reaction.

The reaction is generally carried out at a temperature of 50° C. to 200° C., usually 90° C. to 160° C.

The pressure, which primarily depends on the nature of the starting mono- or polyethylenic hydrocarbons, can be from atmospheric pressure up to 50 bars, for example. Thus, for gaseous ethylenic hydrocarbons under normal conditions, the pressure is between 10 and 50 bars depending on the proportion between the ethylenic hydrocarbon and the alkali metal carbonate or bicarbonate used. The reaction time is 0.5 to 24 hours, for example.

The substances of the invention are liquid substances which generally contain 20% to 70% by weight of sulphur. They are clear and homogeneous even when the sulphur content is high. The color varies depending on the nature of the starting hydrocarbon and the quantity of fixed sulphur. They may be very slightly or slightly coloured (for example with monoethylenic hydrocarbons such as isobutene) to highly colored (for example with polyethylenic hydrocarbons).

With monoethylenic hydrocarbons, the sulphur-containing substances are characterised by a near absence of ethylenic carbon atoms.

The sulphur content of the substances of the invention confers them with antiwear and extreme pressure properties and they can advantageously be used as additives for lubricating oils and greases, in particular for oils for automobile gears and in industrial oils.

For these uses, the substances of the invention are generally incorporated into the lubricating compositions in concentrations of 0.05% to 20%, preferably 0.5% to 10% by weight.

Some of the sulphur-containing substances of the invention, in particular those deriving from the sulphurization of isobutene, can also be used as sulphurization agents, in particular for the preparation of catalysts for use in refining petroleum products.

The following examples illustrate the invention.

EXAMPLES

Example 1

112.5 g (3.51 mole) of sulphur, 22.5 g (0.21 mole) of sodium carbonate, 202 g of water and 36 g (0.642 mole) of isobutene were introduced into a 1 liter reactor which could operate under pressure and which was provided with a stirrer, a system for introducing liquid or gaseous reactants, and a system for controlling the temperature and the pressure. The reaction mixture was heated at 130° C. for 10 hours. The maximum pressure reached was 24 bars. After returning to room temperature, the reaction mixture was extracted with 150 ml of n-heptane. After washing with 10 weight % sodium hydroxide, then washing with water, the n-heptane was evaporated off under reduced pressure and 81 g of a clear liquid was obtained which had a sulphur content of 63.5% by weight.

Example 2

112.5 g (3.51 mole) of sulphur, 22.5 g (0.163 mole) of potassium carbonate, 202 g of water and 36 g (0.642 mole) of isobutene were introduced into a 1 liter reactor which could operate under pressure and which was provided with a stirrer, a system for introducing liquid or gaseous reactants, and a system for controlling the temperature and the pressure. The reaction mixture was heated at 130° C. for 10 hours. The maximum pressure reached was 26 bars. After returning to room temperature, the reaction mixture was extracted with 150 ml of n-heptane. After washing with 10 weight % sodium hydroxide, then washing with water, the n-heptane was evaporated off under reduced pressure and 95.3 g of a clear liquid was obtained which had a sulphur content of 67% by weight.

Example 3

112.5 g (3.51 mole) of sulphur, 22.5 g (0.416 mole) of sodium bicarbonate, 202 g of water and 36 g (0.642 mole) of isobutene were introduced into a 1 liter reactor which could operate under pressure and which was provided with a stirrer, a system for introducing liquid or gaseous reactants, and a system for controlling the temperature and the pressure. The reaction mixture was heated at 130° C. for 10 hours. The maximum pressure reached was 25 bars. After returning to room temperature, the reaction mixture was extracted with 150 ml of n-heptane. After washing with 10 weight % sodium hydroxide, then washing with water, the n-heptane was evaporated off under reduced pressure and 71 g of a clear liquid was obtained which had a sulphur content of 61.3% by weight.

Example 4

50 g (1.56 mole) of sulphur, 15.0 g (0.15 mole) of potassium bicarbonate, 135 g of water and 72 g (1.285 mole) of isobutene were introduced into a 1 liter reactor which could operate under pressure and which was provided with a stirrer, a system for introducing liquid or gaseous reactants, and a system for controlling the temperature and the pressure. The reaction mixture was heated at 130° C. for 10 hours. The maximum pressure reached was 36 bars. After returning to room temperature, the reaction mixture was extracted with 150 ml of n-heptane. After washing with 10 weight % sodium hydroxide, then washing with water, the n-heptane was evaporated off under reduced pressure and 70.5 g of a clear liquid was obtained which had a sulphur content of 64.6% by weight.

Example 5

112.5 g (3.51 mole) of sulphur, 1.2 g (0.0087 mole) of potassium carbonate, 225 g of water and 36 g (0.642 mole) of isobutene were introduced into a 1 liter reactor which could operate under pressure and which was provided with a stirrer, a system for introducing liquid or gaseous reactants, and a system for controlling the temperature and the pressure. The reaction mixture was heated at 130° C. for 10 hours. The maximum pressure reached was 25 bars. After returning to room temperature, the reaction mixture was extracted with 150 ml of n-heptane. After washing with 10 weight % sodium hydroxide, then washing with water, the n-heptane was evaporated off under reduced pressure and 16 g of a clear liquid was obtained which had a sulphur content of 41% by weight.

Example 6

75 g (2.34 mole) of sulphur, 15 g (0.375 mole) of sodium carbonate, 135 g of water, 44.8 g (0.77 mole) of isobutene and 2.6 g (0.046 mole) of 1,3-butadiene were introduced into a 1 liter reactor which could operate under pressure and which was provided with a stirrer, a system for introducing liquid or gaseous reactants, and a system for controlling the temperature and the pressure. The reaction mixture was heated at 130° C. for 12 hours. The maximum pressure reached was 29 bars. After returning to room temperature, the reaction mixture was extracted with 150 ml of n-heptane. After washing with 10 weight % sodium hydroxide, then washing with water, the n-heptane was evaporated off under reduced pressure and 78 g of a clear liquid was obtained which had a sulphur content of 62% by weight.

Example 7

112.5 g (3.51 mole) of sulphur, 22.5 g (0.212 mole) of sodium carbonate, 202 g of water and 36 g (0.32 mole) of diisobutene were introduced into a 1 liter reactor which could operate under pressure and which was provided with a stirrer, a system for introducing liquid or gaseous reactants, and a system for controlling the temperature and the pressure. The medium was heated at 130° C. for 10 hours. The maximum pressure reached was 13 bars. After returning to room temperature, the reaction mixture was extracted with 150 ml of n-heptane. After washing with 10 weight % sodium hydroxide, then washing with water, the n-heptane was evaporated off under reduced pressure and 33 g of a clear liquid was obtained which had a sulphur content of 31% by weight.

C13 NMR examination and elementary analysis of the substances prepared as described in Examples 1 to 7 indicated the absence of ethylenic carbon atoms and the absence of sodium or potassium in all the substances prepared as described in Examples 1 to 7.

Example 8

Examination of the Solubility of the Substances of the Invention

The solubilities of substances of the invention, prepared as described in Examples 1 to 7, were examined in a 130 Neutral Solvent mineral oil and in a synthetic hydrogenated polyalphaolefinic oil (PAO 6), at a concentration which ensured that the sulphur content was kept to 2% by weight. The results are shown in Table I.

Example 9

Characterisation of Extreme Pressure Properties

The extreme pressure properties of the products of the invention, prepared as described in Examples 1, 2, 3, 4 and 6, were examined in a 130 Neutral Solvent mineral oil at a concentration which ensured that the sulphur content due to the additive was kept to 2% by weight. Characterisation was carried out using a 4 ball machine according to standard ASTM D2783. The results are shown in Table II.

TABLE I

| PRODUCT FROM EXAMPLE NO | ADDITIVE/ OIL wt % | S/ OIL wt % | SOLUBILITY/ MINERAL OIL 130 NS | SOLUBILITY/ SYNTHETIC OIL PAO 6 |
|---|---|---|---|---|
| 1 | 3.06 | 2 | yes | yes |
| 2 | 2.99 | " | yes | yes |
| 3 | 3.26 | " | yes | yes |
| 4 | 3.10 | " | yes | — |
| 5 | 4.88 | " | yes | yes |
| 6 | 3.23 | " | yes | — |
| 7 | 6.45 | " | yes | yes |

TABLE II

| PRODUCT FROM EXAMPLE NO | ADDITIVE/ OIL wt % | S/ OIL wt % | 4 BALL MACHINE TESTS | |
|---|---|---|---|---|
| | | | Welding load (daN) | load/wear index (daN) |
| 1 | 3.06 | 2 | 380 | 74 |
| 2 | 2.99 | " | 400 | 80 |
| 3 | 3.26 | " | 440 | 84 |
| 4 | 3.10 | " | 420 | 81 |
| 6 | 3.23 | " | 420 | 80 |

We claim:

1. A process for producing a sulphur-containing product comprising reacting at least one monoethylenic hydrocarbon containing 2 to 36 carbon atoms with elemental sulphur in the presence of (i) at least one alkali metal carbonate or bicarbonate and (ii) water in a proportion in the range 50 to 500 cm$^3$ per ethylenic unsaturation in the starting hydrocarbon, and/or at least one alkyleneglycol.

2. A process according to claim 1, wherein the hydrocarbon consists of a monoethylenic hydrocarbon containing 2 to 36 carbon atoms and 1 to 3 ethylenic unsaturations and the sulfur-containing substance produced contains at least 40% sulfur and is a liquid soluble in lubricants.

3. A process according to claim 2, wherein the sulfur-containing substances produced contain at least 60% sulfur.

4. A process according to claim 1, wherein the sulfur containing substance produced is a liquid soluble in lubricants.

* * * * *